United States Patent [19]
Tomes et al.

[11] Patent Number: 5,879,918
[45] Date of Patent: Mar. 9, 1999

[54] PRETREATMENT OF MICROPROJECTILES PRIOR TO USING IN A PARTICLE GUN

[75] Inventors: Dwight Tomes, Cumming; Margit Ross, West Des Moines, both of Iowa; Leigh Bangs, Carmel, Ind.

[73] Assignee: Pioneer Hi-Bred International, Inc., Des Moines, Iowa

[21] Appl. No.: 157,940

[22] Filed: Nov. 24, 1993

Related U.S. Application Data

[63] Continuation of Ser. No. 769,175, Sep. 30, 1991, abandoned, which is a continuation-in-part of Ser. No. 351,075, May 12, 1989, abandoned.

[51] Int. Cl.⁶ .................................................. C12N 15/00
[52] U.S. Cl. .................................... 435/172.3; 435/172.1; 435/176
[58] Field of Search ................................ 435/172.3, 176, 435/172.1; 514/44; 75/355, 365

[56] References Cited

U.S. PATENT DOCUMENTS

| | | | |
|---|---|---|---|
| 3,130,575 | 4/1964 | Rogers | 73/12 |
| 3,236,634 | 2/1966 | Lambdin et al. | 75/0.5 |
| 3,404,599 | 10/1968 | Annis | 89/1 |
| 4,023,961 | 5/1977 | Douglas et al. | 75/355 |
| 4,762,695 | 8/1988 | Endo et al. | 423/54 |
| 4,945,050 | 7/1990 | Sanford et al. | 435/172.1 |
| 5,240,855 | 8/1993 | Tomes | 435/287 |

OTHER PUBLICATIONS

Sanford, "The Biolistic Process" *Trends in Biotechnology*, vol. 6 (1988), pp. 299–302.

Sanford, et al. "Delivery of Substances Into Cells and Tissue", Particle Science & Technology, vol. 5(1987), pp. 27–37.

"Applied Biosystems" (1986), DNA/RNA Extractor Notes DEN 340A/07 dated Dec. 18, 1986, pp. 1–4.

*Primary Examiner*—Ponnathapura Achutamurthy
*Attorney, Agent, or Firm*—Zarley, McKee, Thomte, Voorhees & Sease

[57] ABSTRACT

An improvement in the process of transporting biological materials into living cells by bombarding the cells with microprojectile particles coated with biological material. In the improved process prior to coating of the particles such as tungsten beads for example, with biological material such as DNA, the particles are first pretreated with a strong inorganic acid such as nitric acid.

18 Claims, No Drawings

PRETREATMENT OF MICROPROJECTILES PRIOR TO USING IN A PARTICLE GUN

This is a continuation of application Ser. No. 07/769,175 filed on Sep. 30, 1991, abandoned, which is a CIP of Ser. No. 07/351,075 filed May 12, 1989, abandoned.

BACKGROUND OF THE INVENTION

This invention relates to an improved process for transferring biological materials such as nucleic acid into the cytoplasm of living cells. With the rapid advancement of recombinant DNA technology, there is a wide-ranging need for biologists to transfer biologic substances from one cell to another, and to transfer synthetic biological material into living cells to exert their activity therein. Such materials can include biological stains, proteins (antibodies or enzymes), and, most commonly, nucleic acids genetic material (either RNA or DNA). Most of the techniques used are painstakingly slow and use methods which transport materials into, at most, only a few cells at a time. More recently, there has been developed a particle bombardment process which utilizes a particle gun, as described in Sanford, et al., 1987, "Delivery of Substances Into Cells and Tissues Using A Particle Bombardment Process," *Journal of Particle Science and Technology* 5:27–37, the disclosures of which are hereby incorporated herein by reference.

An earlier invention of one of the joint inventors, Dwight Tomes, relates to an improved particle gun which uses a gun having a rifled barrel. The disclosure of particle gun bombardment and the method of transport of biological materials such as DNA into living cells as described in Tomes, IMPROVED PARTICLE GUN, filed May 12, 1989, Ser. No. 07/351,075, now abandoned, is incorporated herein by reference.

The effectiveness of particle transport is, of course, measured by the ability of living cells into which the transported particles have been inserted to pick up and express the biological material. This, of course, depends upon a wide variety of conditions. The less the expression, the less successful the transport. Correspondingly, the more successful the expression of the living cells i.e. the extent that they pick up and express the transported biological material, the better the nucleic acid insertion experiments.

In the particle gun technique the biological material (DNA for example) is mixed with the carrier. The carrier generally is comprised of a substantially inert metal in the form of small beads which function as microprojectiles. Generally, the microprojectiles have a diameter within the range of about 1 micron to about 4 microns. These beads can be made from tungsten, palladium, platinum or gold or an alloy thereof. Tungsten is preferred for reasons of economics. However, tungsten generally does not give as good or as successful transport and expression as does gold unless used with the parent pre-treatment process. Beads can generally range from about 1 micron to about 1.5 microns in diameter.

In the most preferred process, the beads are mixed with a small amount of biological material such as DNA or RNA. This is mixed with calcium chloride and a certain amount of polyamine is added.

Generally the ranges of each of these ingredients should be as follows:

Twenty-five $\mu l$ of tungsten particles at a concentration of 15–400 mg in 2 ml sterile water are placed in a sterile 10 ml centrifuge tube and agitated to suspend the beads. The preferred amount of beads is 375 mg/2 ml. Twenty-five $\mu l$ of the suspended tungsten beads are placed in an Eppendorf tube and DNA is added at a concentration of 1 $\mu g/\mu l$ with the amount varying between 1 $\mu l$ and 20 $\mu l$, the preferred amount being 10 $\mu l$. A calcium chloride solution of 25 $\mu l$ and having a concentration between 1.0–4.0M, preferably 2.5M is mixed with the DNA/bead mixture.

While addition of spermidine to the biological material/microprojectile combination has been previously employed, it has now been more broadly discovered that addition of a variety of polyamines to mixtures of tungsten beads and DNA or RNA in preparing microprojectiles significantly improve rates of transformation. While not intending to be limited by theory, it is believed that the polyamine improves delivery of biological material to the cells in this process by improving adherence of the materials to the microprojectile beads. Suitable polyamines have been found to include, for example, spermine, spermidine, caldine, thermine, and the like. The preferred polyamine, spermine, has been found to be superior to the previously disclosed spermidine additive. Accordingly, at this point a polyamine, preferably spermine, in an amount of 10 $\mu l$ and a concentration between 0.05M and 0.5M, preferably at 0.1M is added followed by finger vortexing. This mixture is allowed to stand for 10 minutes prior to centrifugation for one to two minutes at 9,000 rpm. Centrifugation may be used but is not required. The microprojectile mixture forms a pellet at the bottom of the Eppendorf tube. Before use, supernatant is withdrawn from the tube to provide a final volume of 30 $\mu l$.

The DNA/bead mixture is sonicated briefly to suspend the microprojectiles prior to use. The suspended microprojectiles carrying the biological material are transferred to the forward end of the macroprojectile by micropipette in aliquots of 1–5 $\mu l$, with 1.5 $\mu l$ preferred.

Among the difficulties which have been encountered in the past in using microprojectiles is that large masses of DNA would clump onto the particles which make it harder to separate and also make it more likely that the particles will kill the cells during bombardment.

As can be seen, there is therefore a continuing need to develop microprojectile bombardment processes for improved transformation of biological materials into living cells by a process which will not kill the cells during bombardment, by a process which can utilize inexpensive tungsten beads, and by a process can use such lesser expensive beads and still achieve a highly successful transformation and expression. This invention has as its primary objective the fulfillment of this need.

SUMMARY OF THE INVENTION

The invention relates to an improvement in the process of successfully transporting biological material into living cells by bombarding the cells with biological material coated particles. The preferred particles are tungsten and the method of the present invention allows use of the more economical tungsten beads rather than gold. The achievement of the objectives of the present invention is accomplished by pretreating the preferred tungsten beads with a strong inorganic acid, preferably nitric acid.

DETAILED DESCRIPTION OF THE INVENTION

In accordance with the process of this invention prior to coating of the microprojectile beads, they are first pretreated with a strong inorganic acid. The strong inorganic acid is selected from the group consisting of nitric acid, sulfuric acid, hydrochloric acid and phosphoric acid or mixtures thereof. The preferred acid is nitric acid.

The concentration of the strong inorganic acid is not critical. At the lower end, a concentration of as low as 0.01 molar has been used successfully and at the upper end there appears to be only a process economic consideration. Namely excessive amounts are not harmful to the metallurgy or surface of the beads, but there is not reason to use concentrations beyond an amount sufficiently concentrated to effectively clean and pretreat the beads. Generally, the upper limit would be a practical limit of about 1.0 molar, preferably the concentration of the acid would be within the range of 0.1 molar to about 0.5 molar.

The time of treatment is not critical but generally can range from about 5 minutes to about 60 minutes, preferably from about 10 minutes to about 20 minutes. The importance of time is sufficient time for the beads, to successfully contact the nitric acid. In this regard, successful contact is best achieved when beads are agitated during their pretreatment. Preferably the agitation is continuous and most preferably the agitation is by sonication. Following the sonication procedure, the particles, if treated with nitric acid, should not settle out of the liquid suspension if they are clean. Following a 20 minute sonication, the washed particles stayed in suspension, thus it was determined that the 20 minute wash was sufficient for successfully cleaning the tungsten particles. Prior to the nitric acid wash, tungsten immediately fell out of suspension.

The precise beads employed are not critical and the process shows distinct advantages when the beads are any beads selected from the group consisting of tungsten, palladium, platinum and gold or an alloy thereof. Preferably the beads have a diameter of from about 1 micron to about 1.5 micron. The most preferred beads are tungsten since by using the pretreatment of the present invention tungsten can be used as effectively as more expensive metals such as platinum, palladium and gold.

After the pretreatment process of the present invention a variety of conventional steps may be employed. The acid is rinsed from the beads, and the rinse may be a water rinse, for example followed by an alcoholic rinse, for example, followed by ethanol. The beads are then conventionally air dried, perhaps by vacuum speed drying. After this, the biological material such as DNA is added to the microprojectiles and proper mixing is done. Conventional additives is know to be mixed with a biological material such as calcium chloride and a certain amount of amines such as a polyamine. Thereafter the plant tissue is bombarded to achieve the transport of biological material into living cells or simulation therein.

The following examples are offered to illustrate but not necessarily limit the present invention. They demonstrate that with the pretreatment of the present invention tungsten is more effective than gold beads.

EXAMPLE 1

In this example a particle gun experiment tested tungsten and gold after nitric acid was used to clean the surfaces of the particles as a means to reduce flocullation and increase DNA binding.

The purpose was to evaluate the effect of a nitric acid cleaning on tungsten and gold particles prior to drying them in a speed vacuum. They were compared to a standard control.

The genotype material used was an embryonic maize suspension of DNA. The maize suspension medium contained Murashige and Skoog salts: Reference: Murashige, T., Skoog, F.: A Revised Method for Rapid Growth and Bioassays with Tobacco Tissue Cultures, Physiol. Plant. 15:473–497 (1962) with 2.0 mg/L of 2,4-D, which is 2,4-Dichorophenoxy-acetic Acid and 3% sucrose. In addition, the media used involved maize callus medium with the following description: AT salts with 700 mg/L proline, 0.75 mg/L 2,4-D, 3% sucrose. Reference: Tomes, D., Cell Culture, Somatic Embryogenesis and Plant Regeneration in Maize, Rice, Sorghum, and Millets in *Cereal Tissue and Cell Culture*, Nijnoff and Junk, Amsterdam, 1985.

The particle gun treatment involved use of the particle gun as described previously in the incorporated by referenced Tomes application. The beads were tungsten 1.8 um from GTE, tungsten 1.2 um from GE, gold (flakeless) from Engelhard Industries, 25 mg tissue per plate being used. There was a 0.25M mannitol pretreatment, overnight, and there was one bombardment per sample using pDP460 DNA which contains the GUS gene. pDP460 is described in Example 2 below.

The bombardment occurred in the following way. Suspension cells were used one day after subculture and sieved through a 710 um screen and resuspended in maize suspension medium+0.25M mannitol at 50 mg/ml (1 g tissue in 20 ml medium). They were agitated on the shaker overnight. To ready for particle gun treatment, 0.5 ml aliquots were pipetted onto the center of double layers of 617 Whatman grade filter paper to which 1 ml maize suspension medium+ 0.25M mannitol has been added. The cells were concentrated in the center of each plate to maximize exposure to bombardment.

Six repetitions were used for all particle treatments including six repetitions for the standard positive control. Twenty-six samples in total were used. Two independent repetitions of the experiment were completed.

To clean the tungsten and gold particles, we weighed 375 mg particles in 2 ml 0.1M nitric acid. Then we sonicated on ice for 20 minutes using the sonicator set at the minimum to keep the particles suspended. Next we rinsed particles two times using sterile deionized water; on final rinse, we replaced with 1 ml of 95% etOH. This was followed by speed vacuum drying.

All samples received one bombardment by the particle gun.

Following particle gun treatment, we transferred the top filter paper of each sample to maize callus medium. The cells were incubated at 28° Celsius in the dark for 48 hours and then assayed for transient GUS activity.

Forty-eight hours post treatment all samples were sacrificed for the GUS cytochemical assay. Based on transient GUS activity, we compared particle types, particle cleaning and particle sources.

An analysis of variance showed significant differences between microprojectile type (gold, tungsten) and between microprojectile washing treatments in this experiment, however, no statistically significant interaction overall was found between these variables. Using a t-test to analyze each microprojectile type and treatment separately, the only significance found was with the GTE tungsten. This is what was expected as there was such a big discrepancy in performance between tungsten from GTE versus GE. After the nitric acid treatment, the performance of both sources of tungsten are nearly equal.

The following table shows the data for the present tests.

TABLE 1

Beta-glucuronidase cytochemical analysis for transient gene
expression completed 36 hours post treatment.
Genotype: 54-68-5, maize embryogenic suspension
DNA: pPHI460
One bombardment per sample

| Particle Type | Particle Treatment | DNA | N | GUS Cell Groups Min | Mean | Max |
|---|---|---|---|---|---|---|
| Tungsten, GE | EtOH | 460 | 12 | 29 | 137 | 342 |
| Tungsten, GE | Nitric Acid | 460 | 12 | 62 | 217 | 460 |
| Significance = 0.111 | | | | | | |
| Tungsten, GTE | EtOH | 460 | 11 | 3 | 81 | 169 |
| Tungsten, GTE | Nitric Acid | 460 | 12 | 39 | 187 | 440 |
| Significance = 0.023 | | | | | | |
| Gold Flakeless | EtOH | 460 | 12 | 4 | 53 | 122 |
| Gold Flakeless | Nitric Acid | 460 | 12 | 8 | 100 | 259 |
| Significance = 0.119 | | | | | | |

*Significance of particle treatment within particle type was measured using a t-statistic for a small sample size.

The data in Table 1 as described illustrates that first cleaning surfaces of the tungsten particles is an effective means to reduce flocculation and increase DNA binding, in comparison of use in non-nitric acid treated particles in comparison with gold treated or nontreated particles.

EXAMPLE 2

In this example, the process of the present invention, using tungsten pretreated with nitric acid was compared with tungsten beads not pretreated with nitric acid. It also compared with bombardment of cells using non-nitric acid treated tungsten microprojectiles in a particle gun, using the standard protocol recommended and publicly published by DuPont. The DuPont protocol, as published, is as follows:

Weigh 60 mg particles and suspend in 1 ml 100% ethanol. Sonicate. Centrifuge at 10,000 RPM for one minute to pellet particles. Withdraw supernatant of ethanol and replace with 1 ml sterile deionized water. Sonicate. Centrifuge at 10,000 RPM for one minute. After final rinse, resuspend in 1 ml deionized water. Store in the freezer. After preparation DNA coating of the particles can be completed.

Prepare DNA-coated particles in small aliquots within microtubes (each aliquot being enough for three bombardments). Many aliquots can be made at one time. For one aliquot, place 25 µl of the washed particles (ensure complete resuspension) into a microtube, then, sequentially: add 2.5 µl DNA (at µg/µl) and finger vortex five times; add 25 µl of 2.5 $CaCl_2$ and finger vortex five times; and 10 µl of spermidine (0.1M-free base) and finger vortex five times. Let sit for about ten minutes. Spin down for 3 minutes, and discard 40 to 50 µl of the supernatant (this will concentrate the particles and leave just enough for 3 bombardments). Repeat this process for all remaining aliquots.

In this example, the DuPont protocol was compared with the protocol of the present invention, wherein tungsten particles, 1.8µ particles, were prepared in accordance with the following procedure:

Weight 375 mg of 1.8µ tungsten and suspend in 2 ml of 0.1M nitric acid. Sonicate for 20 minutes on ice. Centrifuge at 10,000 RPM for one minute and remove nitric acid. Add 2 ml of sterile deionized water, sonicate briefly then centrifuge, repeat water, rinse two times. Remove water supernatent and add 2 ml of 100% Ethanol. Sonicate to resuspend particles, taking out 25 µl aliquot following each sonication. Place aliquot into individual 1.5 ml Eppendorf tubes. Speed vacuum dry tungsten/ethanol suspension. Store particles at room temperature, covered.

The Pioneer tungsten/DNA precipitation method is as follows: add 10 µl (at 1 µg/µl) DNA to speed vacuum dried tungsten, mix with pipettor. Add 25 µl of 2.5M $CaCl_2$ to tungsten/DNA suspension, mix with pipettor. Add 10 µl to 0.1M spermine to tungsten/DNA/$CaCl_2$ suspension, finger vortex. Allow suspension to stand at room temperature for 15 minutes, then withdraw 15 µl of supernatent. Sonicate suspension prior to aliquoting 1.5 µl aliquots onto macroprojectiles.

The embroyogenic maize suspension 2-122-4 (W23× B73) was used. The culture media and particle bombardment procedures were as outlined in example 1 (see page 9).

The particle preparations prepared on day 1 by the respective methods were sequentially sampled for experiments on days 1, 2, 3, 4, and 5 using particles on day 1. DNA/particle mixing using the respective procedures was done on each day. Sixteen samples for each set of this example were completed. Fourteen were treated with pDP460 DNA. The plasmid pDP460 contains an enhanced promoter spanning nucleotides −421 to +2 of CaMV 35S [R. C. Gardner et al. *Nucleic Acids Res.* 9, 2871 (1981)], a 79-bp Hind III-Sal I fragment from pJII101 spanning the 5' leader sequence of tobacco mosaic virus [D. R. Gallie, D. E. Sleat, J. W. Watts, P. C. Turner, T. M. A. Wilson, *Nucleic Acids Res.* 15, 3257 (1987)], a 579-bp fragment spanning the first intron from maize Adhl-S [E. S. Dennis et al., ibid. 12, 3983 (1984)], and 1870-bp fragment from pRAJ275 spanning the GUS coding sequence [R. Jefferson, S. Burgess, D. Hirsh, *Proc. Natl. Acad. Sci. U.S.A.*, 83, 8447 (1986)] and a 281-bp fragment containing a polyadenylation site from the *Agrobacterium tumefaciens* nopaline synthase gene [M. Bevan, W. M. Barnes, M. D. Chilton, *Science II*, 369 (1983)] in pUC18 [C. Yanisch-Perron, J. Vieira, J. Messing, *Gene* 33, 103 (1985)]. The remaining two samples were nontreated controls. All treated samples received one bombardment by the particle gun. Immediately following bombardment all samples were transferred to maize suspension medium and were maintained in the dark at 28° C. for 36 hours.

Thirty-six hours post treatment, all samples were sacrificed for GUS cytochemical assay. Individual cells which stain positive for GUS for both the invention and for the DuPont protocol were recorded. Overall, gene expression for each treatment for each day was compared by establishing a ration between the invention process and the DuPont protocol, with the DuPont protocol not showing any pretreatment with nitric acid. The following Table 2 sets forth the results.

TABLE 2

| Treatment | | | GUS individual cells | | | Ratio |
|---|---|---|---|---|---|---|
| Day | N | Protocol | Min | Mean | Max | INV/DuPont |
| Day 1 | 7 | Invention | 339 | 452 | 572 | 1.7:1.0 |
|  | 7 | DuPont | 173 | 274 | 319 |  |
| Day 2 | 7 | Invention | 207 | 258 | 292 | 1.8:1.0 |
|  | 7 | DuPont | 84 | 146 | 180 |  |
| Day 3 | 7 | Invention | 148 | 211 | 301 | 2.9:1.0 |
|  | 7 | DuPont | 4 | 73 | 100 |  |
| Day 4 | 7 | Invention | 228 | 380 | 485 | 3.5:1.0 |
|  | 7 | DuPont | 8 | 110 | 194 |  |
| Day 5 | 7 | Invention | 62 | 217 | 389 | 2.4:1.0 |
|  | 7 | DuPont | 0 | 91 | 137 |  |

The data of significance in Table 2 is the data under ratio of "INV" to DuPont. There, it is shown that the GUS gene (pDP460) is successfully delivered and expressed in the cells, as measured by the cells turning blue in a much higher ratio, with the process of the present invention than with the standard DuPont process which utilizes similar tungsten particles, but does not pretreat with nitric acid.

EXAMPLE 3

In this example, a comparison of the process of the present invention using nitric acid pretreated beads in the manner described in Example 2 and using tungsten beads which were not pretreated according to the standard DuPont protocol, were prepared precisely as above described. The example was run to show not only successful transport into the cells, but whether or not the DNA after transport is integrated into plant DNA such that cell division carrying the foreign DNA occurs. In other words, can you not only transfer the DNA into the cells, but having done that, can you successfully grow up a plant, which has the foreign DNA integrated into the plant DNA. In this example, standard procedure prenitric acid treated tungsten beads were used with the plant material being Xanthi tobacco cotyledons. The DNA expressed was pDP456 [NPTII+ GUS]. The plasmid pDP456 contains two different plant transcription units (PTU's). The first PTU includes an enhanced promoter spanning nucleotides −421 to +2 of CaMV 35S with the region from −421 to −90 duplicated in tandem [R. C. Gardner et al., Nucleic Acids Res. 9, 2871 (1981)], a 79-bp Hind III-Sal I fragment from pJII101 spanning the 5' leader sequence of tobacco mosaic virus [D. R. Gallie, D. E. Sleat, J. W. Watts, P. C. Turner, T. M. A. Wilson Nucleic Acids Res. 15, 3257 (1987)], an 1870-bp fragment from pRAJ275 spanning the GUS coding sequence [R. Jefferson, S. Burgess, D. Hirsh, Proc. Natl. Acad. Sci. U.S.A. 83, 8447 (1986)] and a 281-bp fragment containing a polyadenylation site from the Agrobacterium tumefaciens nopaline synthase gene [M. Bevan, W. M. Barnes, M.-D. Chilton, ibid. 11, 369 (1983)] in pUC18 [C. Yanisch-Perron, J. Vieira, J. Messing, Gene 33, 103 (1985)]. The second PTU is identical to the first, except that it includes the NPTII coding sequence [R. T. Frayley et al., Proc. Natl. Acad. Sci. U.S.A. 80, 4803 (1983)] in place of GUS. In accordance with this example four in vitro grown Xanthi cotyledons were prepared and bombarded as described in Tomes et al. Plant Mol. Biol. 14: 261–268 (1990).

Two independent experiments were completed in which cotyledons were bombarded for each microprojectile/DNA protocol.

The microprojectile/DNA DuPont comparison treatments were made using the earlier described standard DuPont protocol. The treatments of the present invention were as described in the previous example. All DNA samples received one bombardment by the particle gun. After particle gun treatment, all DNA treated samples were transferred to a selection medium as described in the Tomes, et al. publication.

The number of colonies recovered with each treatment were recorded, and Table 3 indicates NPTII enzyme assays confirmed stable integration of pH1456 in each sample noted as NPTII+.

Table 3 shows the assay results for independent transgenes from the process protocol or the DuPont protocol.

TABLE 3

| Sample  | DNA | Protocol  | NPTII |
|---------|-----|-----------|-------|
| 25,C1   | 456 | Invention | +     |
| 52,C1   | 456 | Invention | +     |
| 52,C2   | 456 | Invention | −     |
| 20,C1   | 456 | Invention | +     |
| 26,C1   | 456 | Invention | +     |
| 26,C2   | 456 | Invention | −     |
| 26,C3   | 456 | Invention | +     |
| 26,C4   | 456 | Invention | +     |
| 55,C1   | 456 | Invention | +     |
| 50,C1   | 456 | Invention | +     |
| 10,C1   | 456 | DuPont    | +     |
| 12,C1   | 456 | DuPont    | +     |
| 14,C1   | 456 | DuPont    | +     |
| 14,C2   | 456 | DuPont    | +     |
| 2,C1    | 456 | DuPont    | +     |
| 41,C1   | 456 | DuPont    | −     |
| 43,C1   | 456 | DuPont    | +     |
| 34,C1   | 456 | DuPont    | +     |
| CONTROL | —   | —         | −     |
| CONTROL | —   | —         | −     |

Out of all the samples treated with the process protocol of the present invention and expendables, 80% of the cotyledons recovered stably transformed colonies. From all samples treated with the DuPont DNA protocol, 6% of the cotyledons recovered stably transformed colonies. The process of the present invention showed a higher number of transformation.

EXAMPLE 4

Example 4 was run to confirm if nitric acid treatment resulted in an increase in transformation with the DuPont protocol compared with the protocol of the present invention. In this example, the material used was genotype 2-122-4 (W23×3) embryogenic maize suspension. The DNA was pDP460. In the particle gun treatments, the process of the present invention was employed using a nitric acid treatment and compared with the DuPont DNA/particle mixing protocol, and the DuPont protocol using nitric acid as the only variance. The methodology was as Example 1.

Forty samples were completed for this example. They were treated with the pDP460 DNA and 20 samples for each method were tested. All treated samples received one bombardment by the particle gun.

The standard protocol for mixing DNA/particles described in Example 2 and of the DuPont method as described in Example 2 were then followed. Following the particle gun treatment, all samples were transferred to maize callus medium and maintained in the dark at 28° C.

Thirty-six hours post-treatment, all samples were sacrificed for GUS cytochemical assay. Thereafter, the transient gene expression was compared between the two treatments based on the number of visible blue stained cells present in each sample. The data is summarized in the following Table 4.

TABLE 4

|                     |    | GUS individual cells | | | Coefficient  |
|---------------------|----|-----|-------|-----|--------------|
| Protocol            | N  | Min | Mean  | Max | of Variation |
| DuPont Original     | 20 | 113 | 326.2 | 491 | 25.19%       |
| Invention Standard  | 20 | 203 | 430.9 | 728 | 29.61%       |

In Table 4 it can be seen that statistically significant differences (letters denote statistical difference at 95% confidence using analysis of variance) were found between the DuPont protocol and the protocol of the present invention in this experiment. These results are in accord with earlier experiments showing that indeed the nitric acid pretreatment allows much higher transient gene expression.

What is claimed is:

1. In the process of transporting biological materials into living cells by bombarding the cells with biological material coated metal bead particles, the improvement comprising:

pretreating and cleaning the metal bead particles with a strong inorganic acid rinsing the acid from said particles, and thereafter coating said bead particles with biological material.

2. The process of claim 1 wherein the strong inorganic acid is selected from the group consisting of nitric acid, sulfuric acid, hydrochloride acid and phosphoric acid.

3. The process of claim 2 wherein the acid is nitric acid.

4. The process of claim 3 wherein the nitric acid has a concentration of from 0.1M to 1.0M.

5. The process of claim 4 wherein the nitric acid has a concentration of from 0.1M to 0.5M.

6. The process of claim 1 wherein the particles are beads selected from the group consisting of tungsten, palladium, platinum, and gold or an alloy thereof.

7. The process of claim 6 wherein the beads are tungsten beads.

8. The process of claim 6 wherein the beads have a diameter of from about 0.5 microns to about 3.0 microns.

9. The process of claim 7 wherein the particles are agitated while being pretreated.

10. The process of claim 9 wherein agitation is by sonication.

11. The process of claim 9 wherein agitation is for from about 5 minutes to about 60 minutes.

12. The process of claim 11 wherein agitation is for from about 10 minutes to about 20 minutes.

13. The process of claim 1 wherein the biological material is DNA.

14. The process of claim 1 wherein the biological material is RNA.

15. An improved process for successful transport of DNA into living cells, said method comprising:

pretreating tungsten projectile beads with a cleaning effective amount of nitric acid; and thereinafter rinsing the nitric acid pretreatment tungsten beads; and then coating the just pretreated tungsten beads with DNA, and accelerating the DNA coated tungsten beads into living target cells.

16. The process of claim 15 wherein the beads are continually agitated during the pretreatment.

17. The process of claim 16 wherein the nitric acid is at a molar concentration of from 0.1M to 0.5M.

18. The process of claim 17 wherein the beads are agitated by sonication.

* * * * *